United States Patent [19]

Nakano et al.

[11] Patent Number: 4,992,570

[45] Date of Patent: Feb. 12, 1991

[54] UCN-1028A AND UCN-1028C AND PROCESS FOR THE PRODUCTION THEREOF

[75] Inventors: Hirofumi Nakano; Eiji Kobayashi; Isami Takahashi; Katsuhiko Ando, all of Machida; Mayumi Yoshida, Sagamihara; Shiro Akinaga, Shizuoka; Takao Iida, Tama, all of Japan

[73] Assignee: Kyowa Hakko Kogyo Co., Ltd., Tokyo, Japan

[21] Appl. No.: 173,174

[22] Filed: Mar. 24, 1988

[30] Foreign Application Priority Data

Mar. 26, 1987 [JP] Japan .................................. 62-72378
Jul. 9, 1987 [JP] Japan ................................. 62-171988

[51] Int. Cl.$^5$ ..................... C07C 50/10; C07C 50/00; C12P 15/00; C12N 1/14
[52] U.S. Cl. ................................... 552/295; 435/127; 435/911; 435/254
[58] Field of Search .................... 260/396 R; 435/127, 435/911, 254; 552/295

[56] References Cited

PUBLICATIONS

Laskin et al., "Handbook of Microbiology", vol. III, 1973, p. 255.
Nakano et al., "UCN-1028A . . . ", J. Antibiotics, 1989, 42(1), pp. 153–155.
Kobayashi et al., "Calphostin C (UCN-1028C) . . . ", Biochem. Biophys. Res. Commun., 1989, 159(2), pp. 548–553.
Arnone et al., "Secondary Mold Metabolites . . . ", Phytochemistry, 1988, 27(6), pp. 1675–1678.
Agricultural and Biological Chemistry 39, 1683 (1975), "Phleichrome, . . . ".

Primary Examiner—Elizabeth C. Weimar
Assistant Examiner—Irene Marx
Attorney, Agent, or Firm—Michael N. Meller

[57] ABSTRACT

UCN-1028A and UCN-1028C having an anti-tumor activity and a protein kinase C inhibitory activity are produced by culturing a microorganism belonging to the genus Cladosporium.

3 Claims, 10 Drawing Sheets

UCN-1028A AND UCN-1028C AND PROCESS FOR THE PRODUCTION THEREOF

BACKGROUND OF THE INVENTION

The present invention relates to UCN-1028A and UCN-1028C and a process for the production thereof.

UCN-1028A and UCN-1028C have an anti-tumor activity, a protein kinase C inhibitory activity, etc. and are useful as anti-tumor agents, carcinosuppressive agents, etc. As a substance which is structurally analogous to UCN-1028A and UCN-1028C, there is known Phleichrome isolated as a plant poison from *Cladosporium phlei* which causes spots on pastures [Agricultural & Biological Chemistry, 39, 1683 (1975), J. Jap. Pasture, 28 (4), 426 (1983)].

SUMMARY OF THE INVENTION

The present invention provides novel compounds UCN-1028A and UCN-1028C, which have an anti-tumor activity, a protein kinase C inhibitory activity, etc. and are useful as anti-tumor agents, carcinosuppressive agents, etc.

UCN-1028A and/or UCN-1028C can be prepared by culturing a UCN-1028A and/or UCN-1028C-producing strain belonging to the genus *Cladosporium* in a medium.

DETAILED DESCRIPTION OF THE INVENTION

The novel compounds UCN-1028A and UCN-1028 C having an anti-tumor activity and a protein kinase C inhibitory activity are represented by the following general formula:

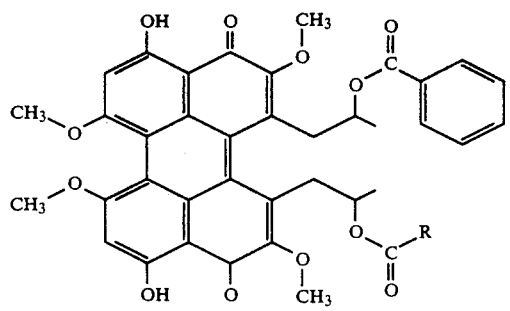

wherein R represents 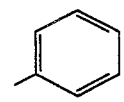 (UCN-1028A) or

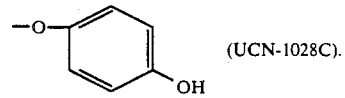 (UCN-1028C).

The physicochemical properties, the physiological activities and the anti-tumor activities of UCN-1028A and UCN-1028C are shown below.

(A) Physicochemical properties of UCN-1028A (1) Molecular formula: $C_{44}H_{38}O_{12}$ (2) Molecular weight: 758

Figure 1:
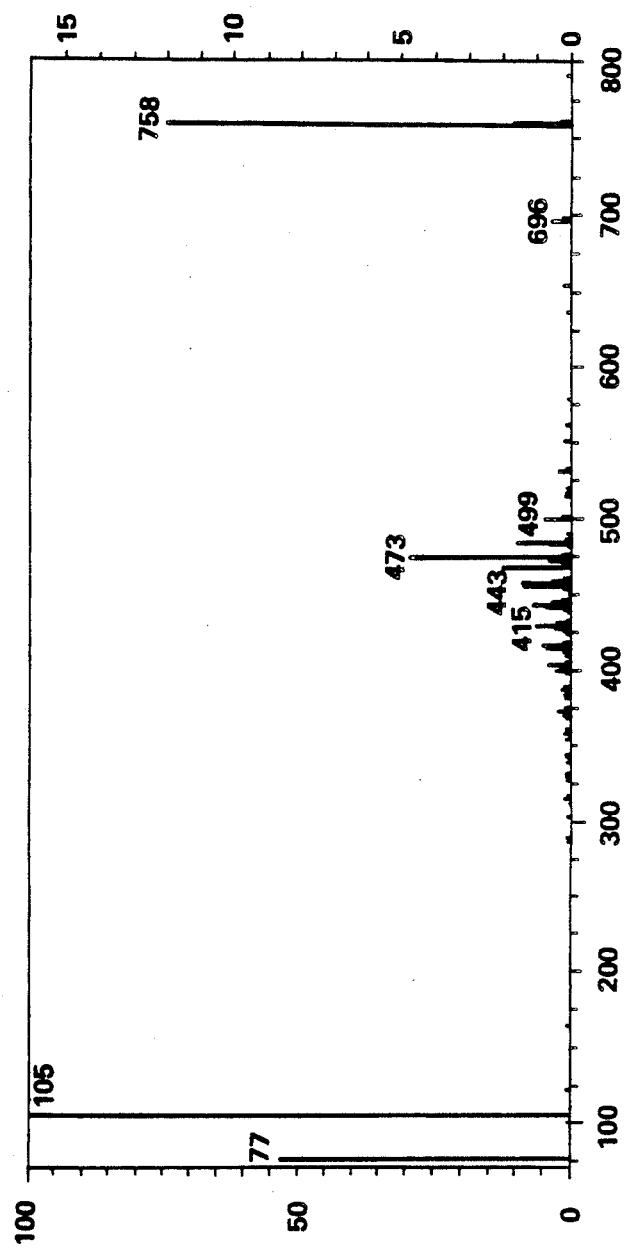
FIG. 1 shows the EI mass spectrum of UCN-1028A.

(3) Mass spectrum: EI mass spectrometry, shown in FIG. 1

Figure 2:
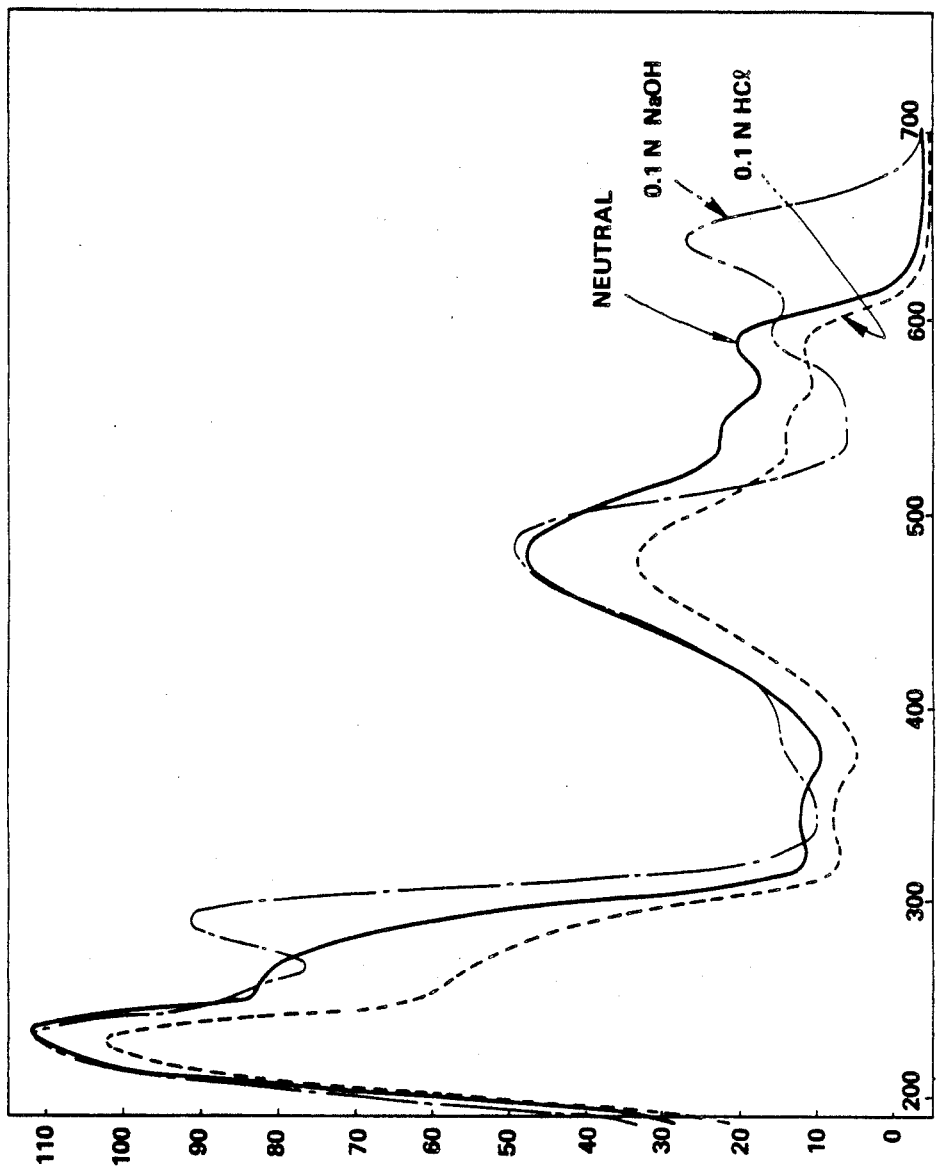
FIG. 2 shows the UV absorption spectrum of UCN-1028A.

(4) UV absorption spectrum: shown in FIG. 2 (measured in MeOH)

Figure 3:
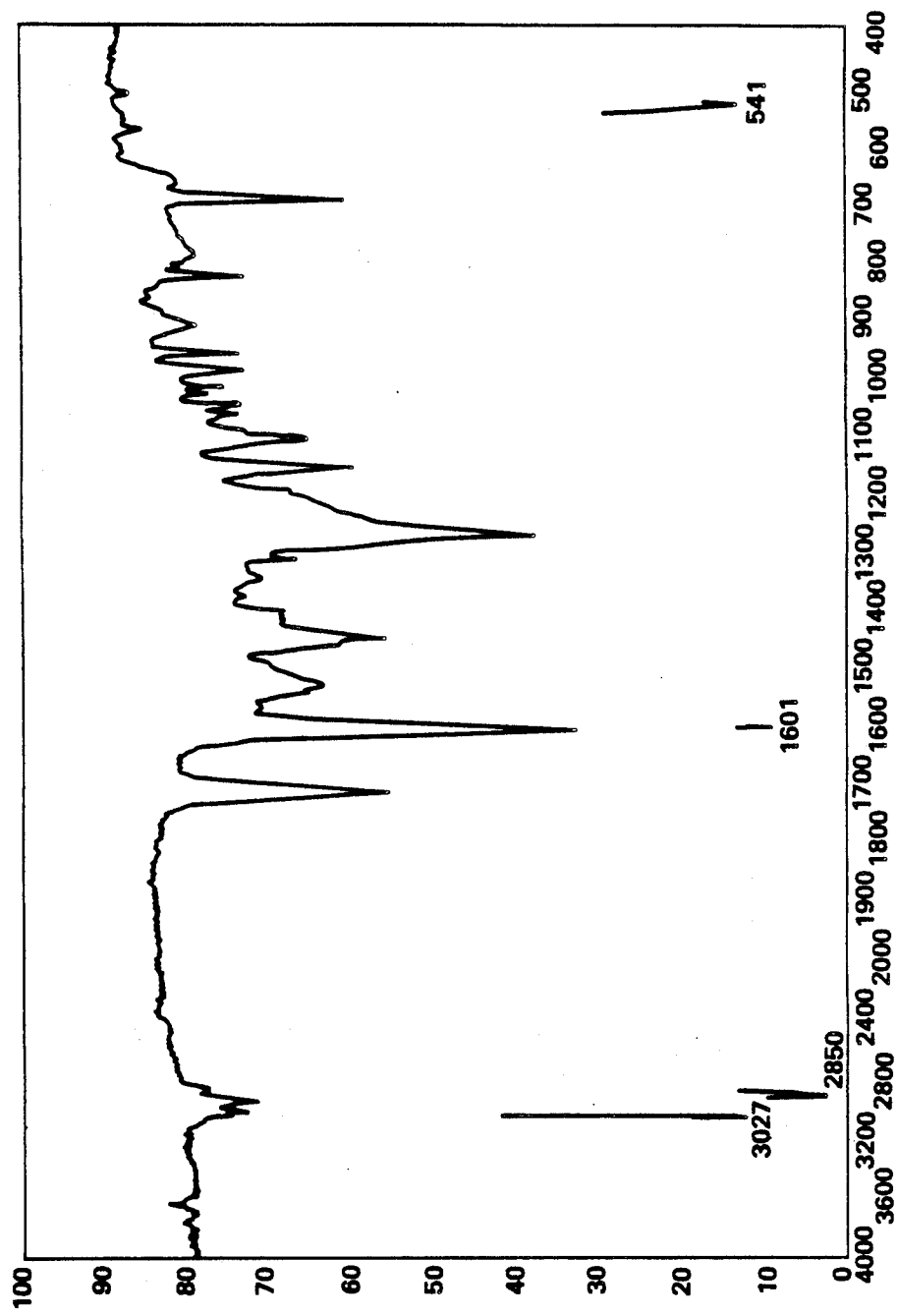
FIG. 3 shows the IR absorption spectrum of UCN-1028A.

(5) IR absorption spectrum: shown in FIG. 3 (measured in $CHCl_3$)

(6) Solubility: insoluble in water; soluble in alkaline water, methanol, acetone and n-hexane; readily soluble in chloroform and ethyl acetate (7) $^1$H-NMR spectrum: (measured at 400 MHz in $CDCl_3$, internal standard TMS); δ(ppm) 1.3 (d, 6H), 3.2 (m, 2H), 3.7 (m, 2H), 3.8 (s, 6H), 4.3 (s, 6H), 5.0 (m, 2H), 6.2 (s, 2H), 6.9 (m, 8H), 7.2 (m, 2H), 15.9 (s, 2H)

Figure 4:
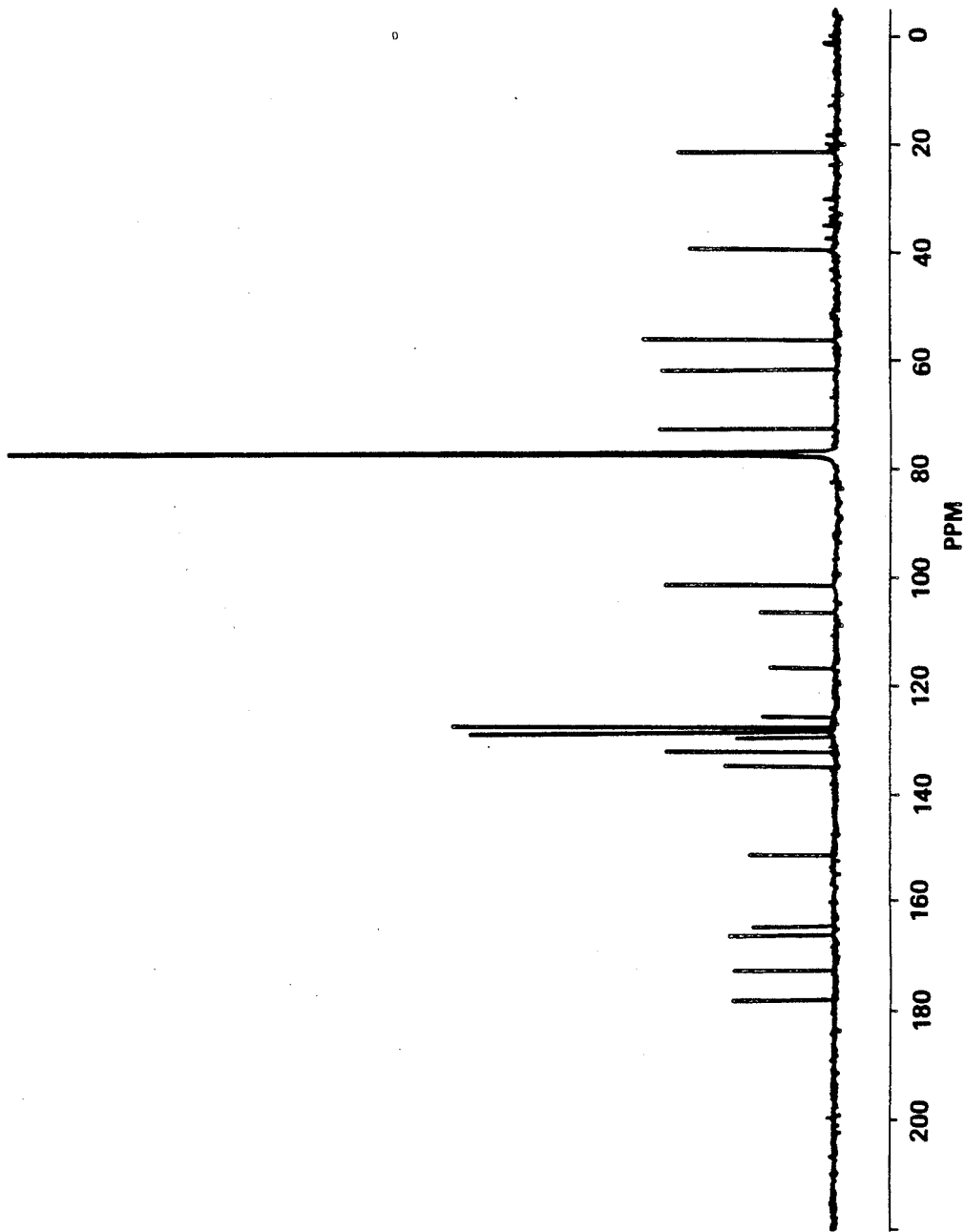
FIG. 4 shows the $^{13}$C-NMR spectrum of UCN-1028A.

(8) $^{13}$C-NMR spectrum: (measured at 400 MHz in $CDCl_3$, internal standard TMS); δ(ppm), shown in FIG. 4

(9) Thin layer chromatography: Rf is 0.60 by silica gel TLC (Art 5715, manufactured by E. Merck) with a chloroform:methanol (97:3 v/v) developing system.

Figure 5:
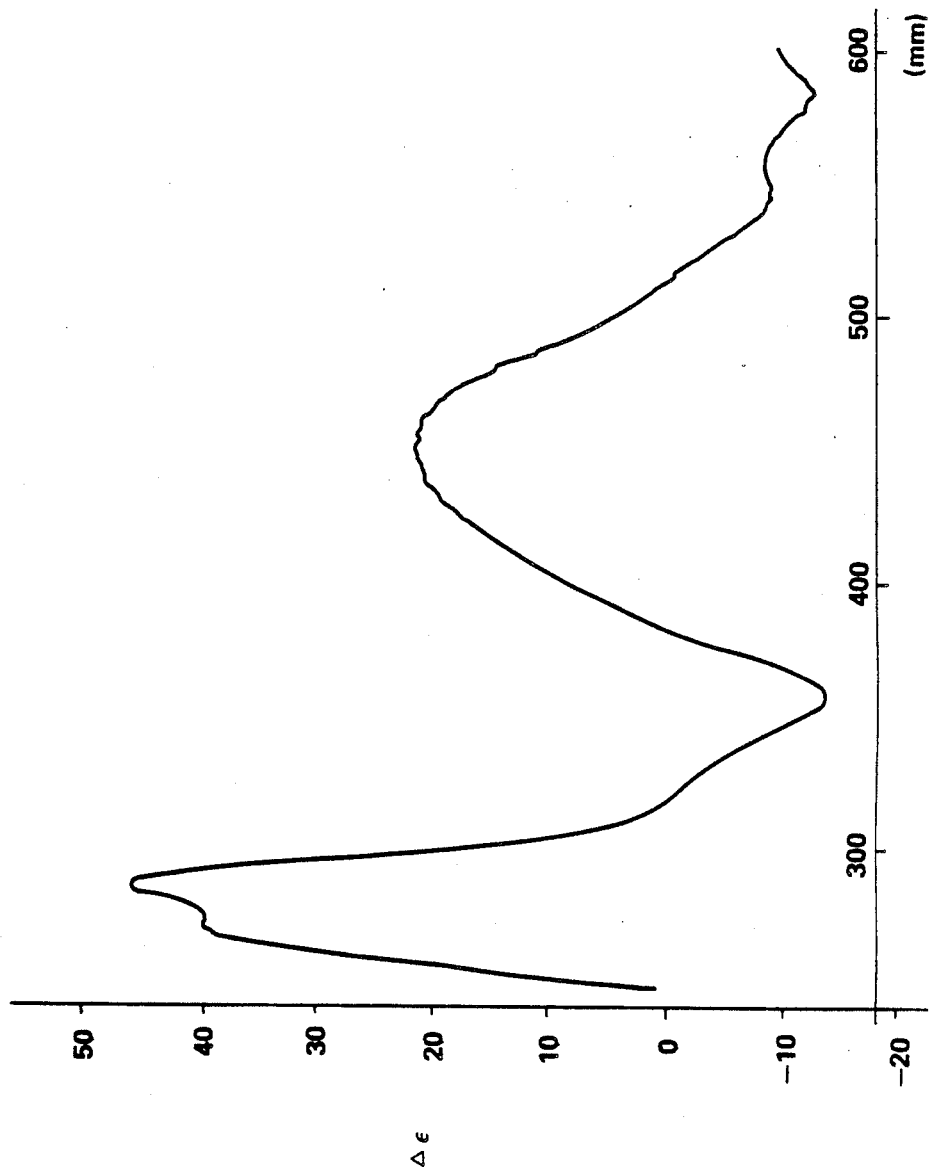
FIG. 5 shows the CD spectrum of UCN-1028A.

(10) CD spectrum: shown in FIG. 5 (measured in MeOH)

(B) Physicochemical properties of UCN-1028C (1) Molecular formula: $C_{44}H_{38}O_{14}$ (2) Molecular weight : 790

Figure 6:
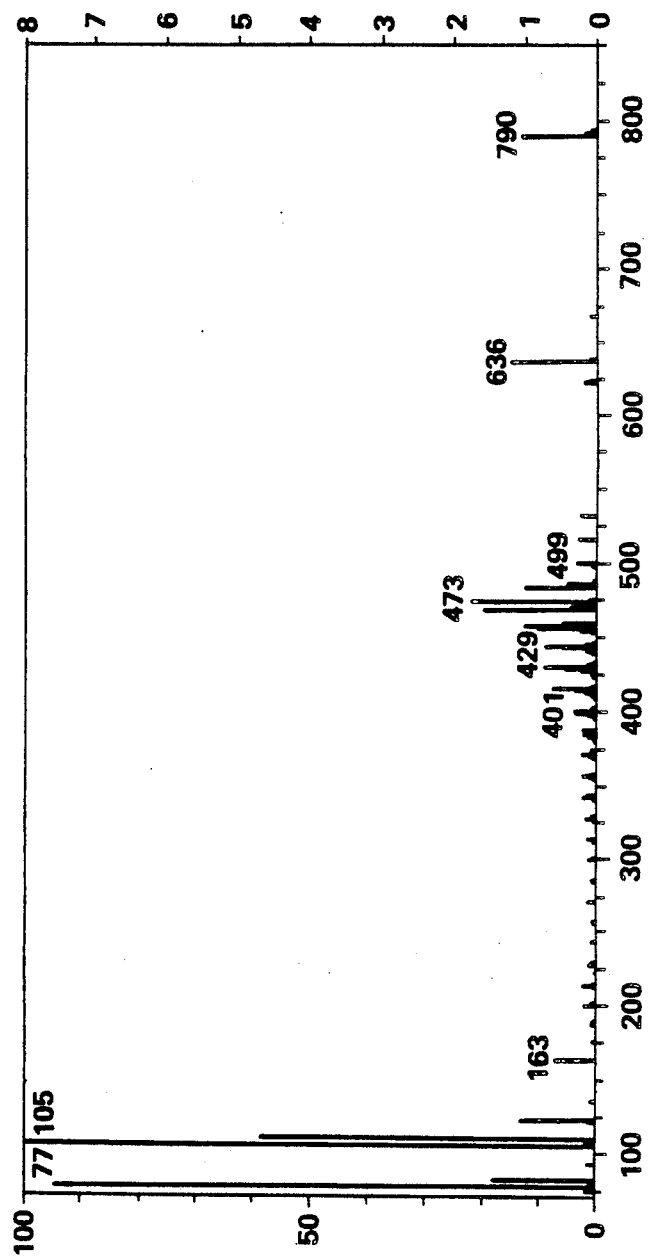
FIG. 6 shows the EI mass spectrum of UCN-1028C.

(3) Mass spectrum: EI mass spectrometry, shown in FIG. 6

Figure 7:
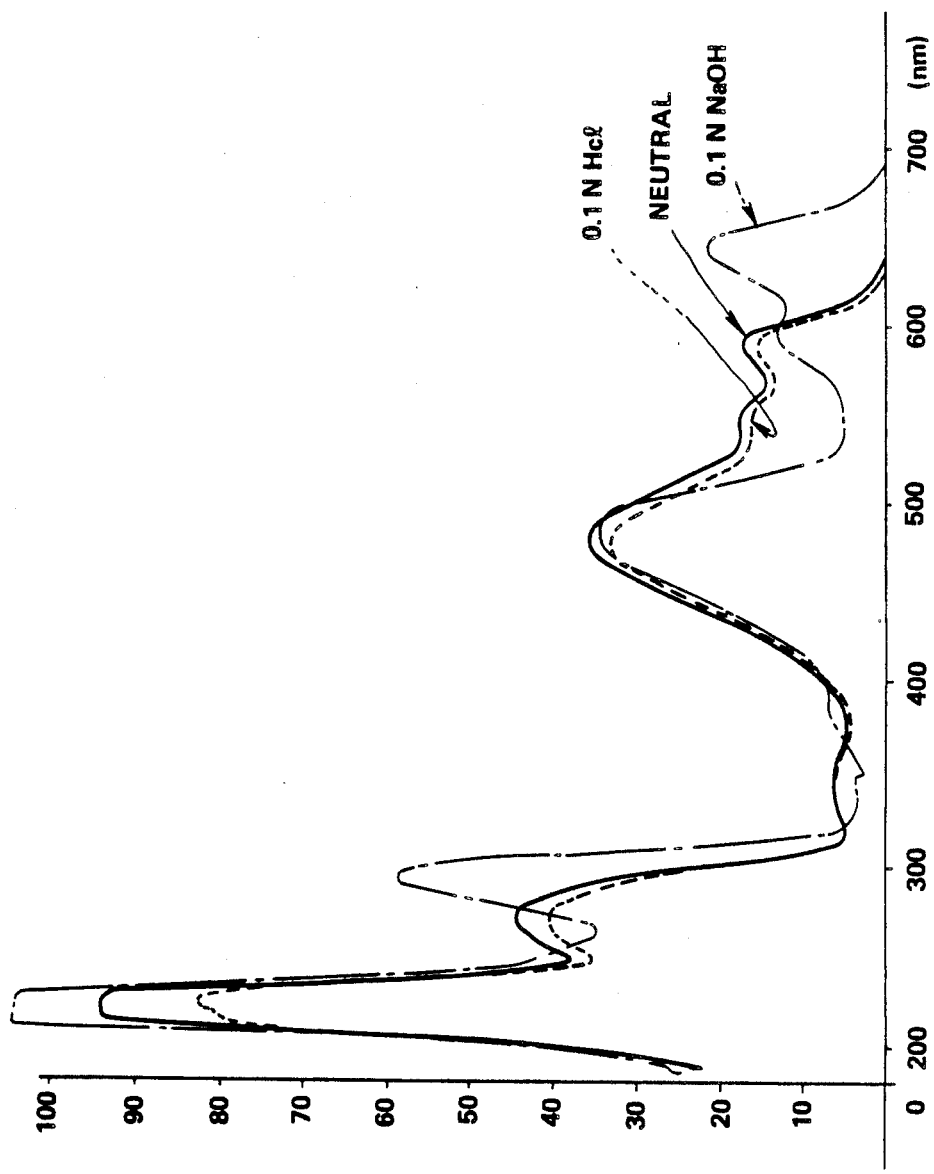
FIG. 7 shows the UV absorption spectrum of UCN-1028C.

(4) UV absorption spectrum: shown in FIG. 7 (measured in MeOH)

Figure 8:
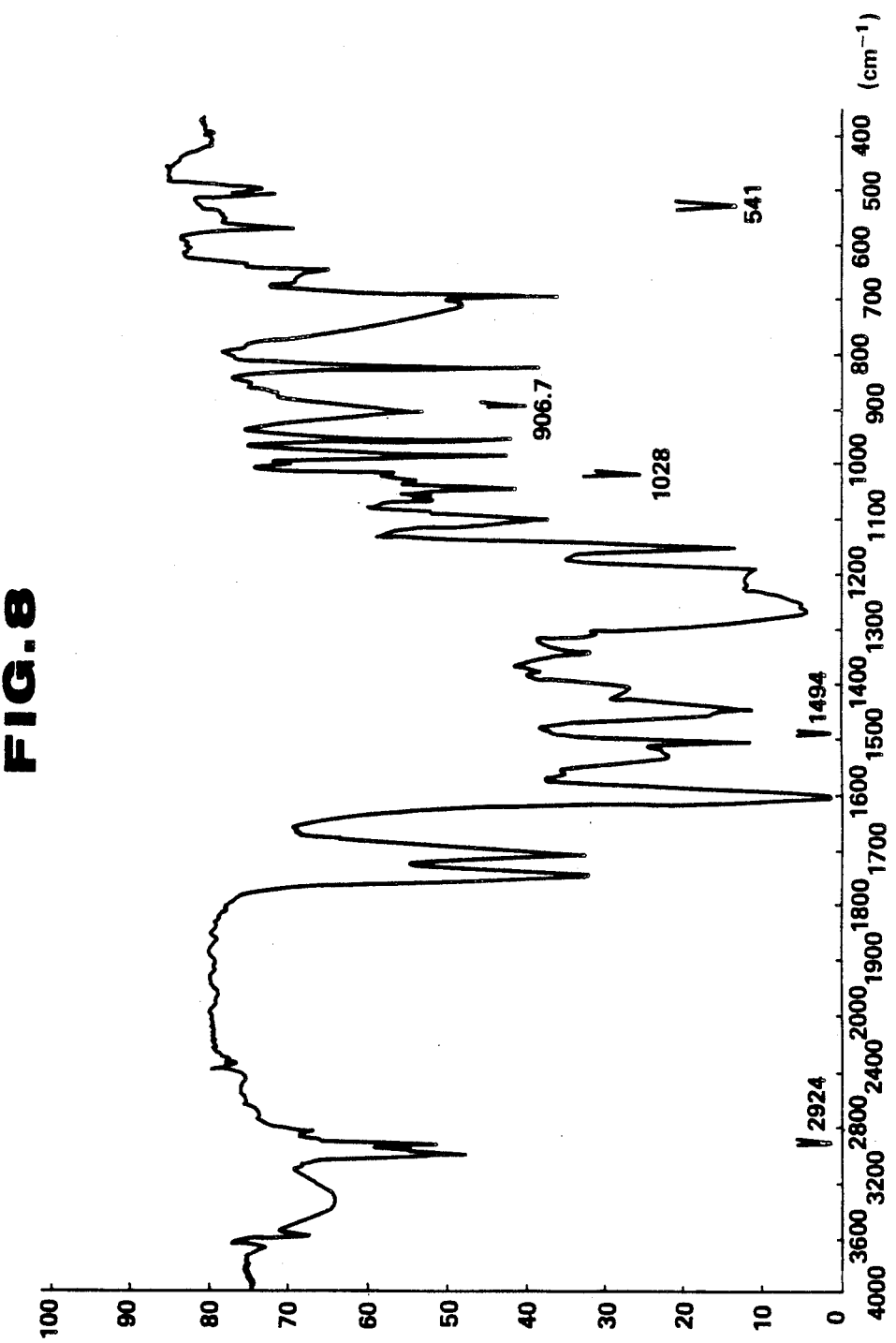
FIG. 8 shows the IR absorption spectrum of UCN-1028C.

(5) IR absorption spectrum: shown in FIG. 8 (measured in $CHCl_3$)

(6) Solubility: insoluble in water; soluble in alkaline water, chloroform, acetone and ethyl acetate; readily soluble in methanol and DMSO (7) $^1$H-NMR spectrum: (measured at 400 MHz in $CD_3OD$, internal standard TMS; δ(ppm) 1.10 (d, 3H, J=6.3 Hz), 1.22 (d, 3H, J=6.3 Hz), 3.00 (dd, 1H, J=9.8, 13.5 Hz), 3.11 (dd, 1H, J=10.1, 13.5 Hz), 3.60 (dd, 1H, J=2.5, 13.5 Hz), 3.62 (dd, 1H, J=1.8, 13.5 Hz), 3.64 (s, 3H), 3.82 (s, 3H), 4.18 (s, 3H), 4.19 (s, 3H), 4.7 (m, 1H), 5.0 (m, 1H), 5.87 (d, 2H, J=8.9 Hz), 6.30 (s, 1H), 6.31 (s, 1H), 6.36 (d, 2H, J=8.9 Hz), 6.74 (dd, 2H, J=8.1, 1.2 Hz), 6.86 (t, 2H, J=8.1 Hz), 7.22 (dt, 1H, J=8.1, 1.2 Hz)

Figure 9:
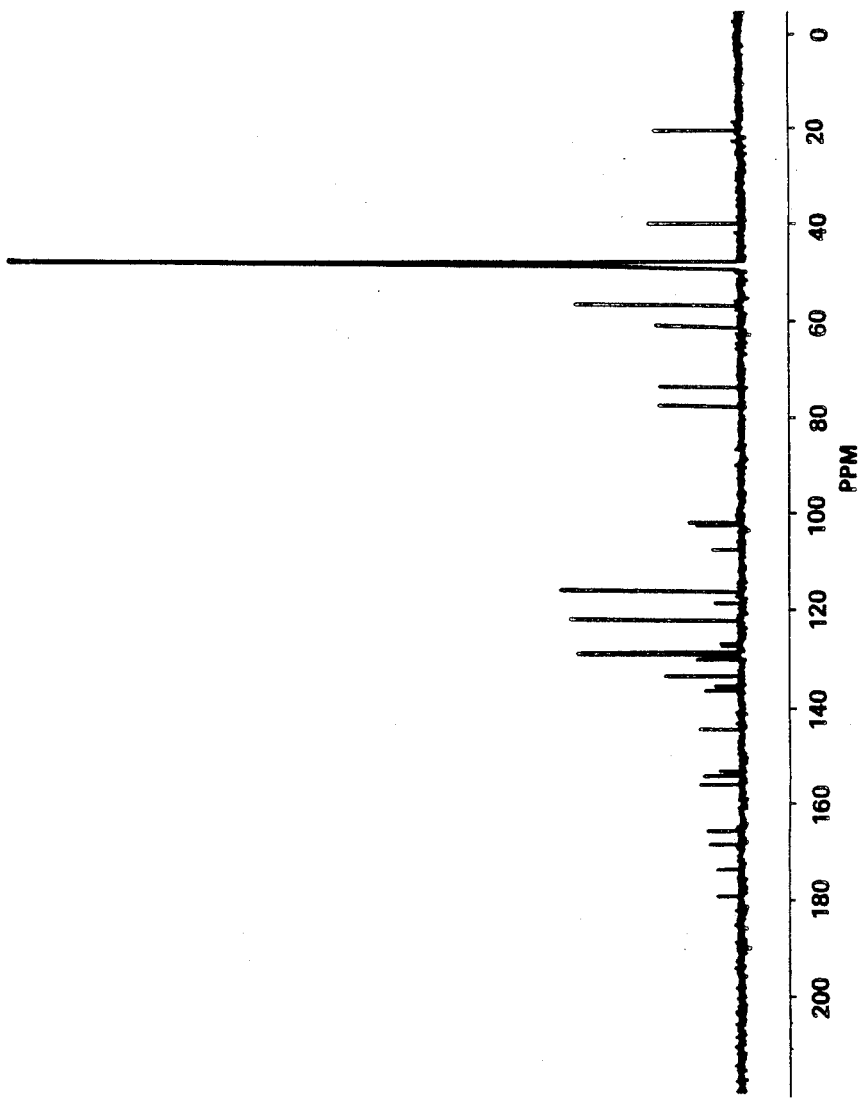
FIG. 9 shows the $^{13}$C-NMR spectrum of UCN-1028C.

(8) $^{13}$C-NMR spectrum: (measured at 400 MHz in $CDCl_3$, internal standard TMS; δ(ppm), shown in FIG. 9

(9) Thin layer chromatography: Rf is 0.3 by silica gel TLC (Art 5715, manufactured by E. Merck) with a chloroform : methanol (97:3 v/v) developing system.

Figure 10:
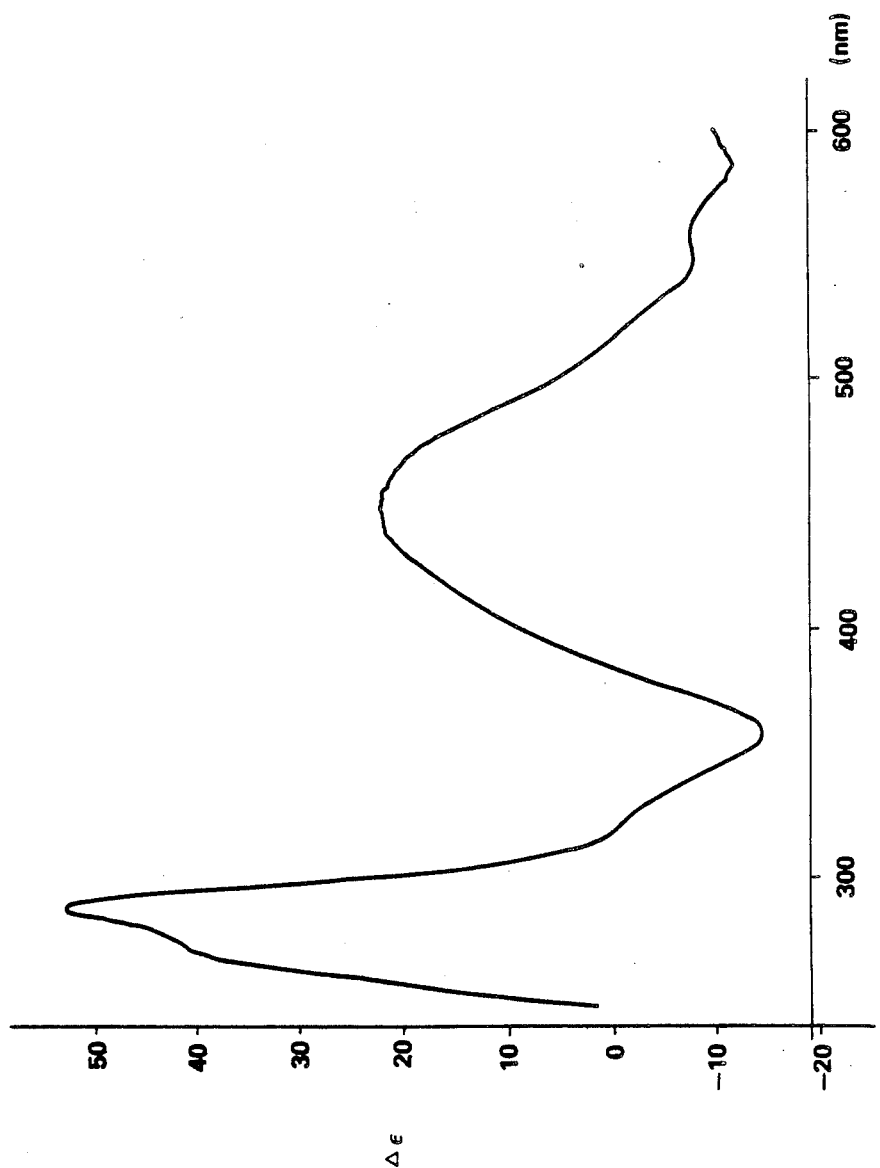
FIG. 10 shows the CD spectrum of UCN-1028C.

(10) CD spectrum: shown in FIG. 10 (measured in MeOH)

(C) Physiological activities of UCN-1028A and UCN-1028C (1) Protein kinase C inhibitory activity Protein kinase C inhibitory activity was measured by the method of Kikkawa, et al. [Journal of Biological Chemistry, 257, 13341 (1982)].

That is, 10 μl of a test solution containing UCN-1028A, UCN-1028C or Phleichrome was added to 250 μl of a solution containing 2.5 μmoles of magnesium acetate, 50 μg of Histone Type IIS (manufactured by Sigma Co., Ltd.), 20 μg of phosphatidyl serine, 0.8 μg of diolein, 25 nmoles of $CaCl_2$, 5 μg of crude enzyme (partially purified from rat brain according to the method of Kikkawa, et al.) and 5 μmoles of Tris-hydrochloride buffer (H 7.5), followed by incubation at 30° C. for 3 minutes. Then, phosphorylation was initiated by addition of 1.25 nmoles of [$\gamma$-$^{32}$P]ATP (5 to $10 \times 10^3$ cpm/nmole), followed by incubation at 30° C. for 3 minutes. The reaction was stopped by adding 25% trichloroacetic acid (TCA), and the reaction solution was filtered through a cellulose acetate membrane (pore size of 0.45 μm) (manufactured by Toyo Filter Paper Co., Ltd.). After the membrane was washed four times with 5% TCA, radioactivity remaining on the membrane was measured. As a control, the same procedure as above was repeated without addition of the test solution and radioactivity was likewise measured. A concentration of the test solution showing 50% inhibition as compared with the control was expressed as $IC_{50}$.

The results are shown in Table 1.

(2) Protein kinase A inhibitory activity

Protein kinase A inhibitory activity was measured according to the method of Kuo, et al. [Biochemistry, 64, according to the method of Kuo, et al. [Biochemistry, 64, 1349 (1969)].

That is, 10 μl of a test solution was added to 250 μl of a solution containing 5 μmoles of Tris-hydrochloride buffer (pH 6.8), 2.5 μmoles of magnesium acetate, 100 μg of Histone Type IIS (manufactured by Sigma Co., Ltd.), 0.25 nmoles of C-AMP and 200 μg of crude enzyme (partially purified from calf heart according to the method of Kuo, et al.). Subsequent procedures were conducted in a manner similar to the case of measuring protein kinase C inhibitory activity described above to determine $IC^{50}$. The results are shown in Table 1.

TABLE 1

| Test Compound | $IC_{50}$ (μg/ml) | |
|---|---|---|
| | Protein Kinase C | Protein Kinase A |
| UCN-1028A | 0.19 | >40 |
| UCN-1028C | 0.07 | >40 |
| Phleichrome | 5.5 | 33 |

UCN-1028A and UCN-1028C have a selective inhibitory activity on protein kinase C, as compared with Phleichrome.

(D) Anti-tumor activity (1) MCF 7 cells

MCF 7 cells ($4.5 \times 10^4$ cells/ml) prepared in a medium comprising RPMI 1640 medium (manufactured by Gibco Co., Ltd.), 10% fetal calf serum, 10 μg/ml insulin and $10^{-8}$M estradiol (hereinafter referred to as medium A) were put into wells of a 96 well microtiter plate in the amount of 0.1 m( per each well. After culturing at 37° C for 20 hours in a carbon dioxide gas incubator, each test solution appropriately diluted with medium A (0.05 ml) was added thereto. Then, culturing was carried out at 37° C. for an hour in the carbon dioxide gas incubator, and the culture supernatant was removed. After the residue was washed once with ProS (composition: 8 g/l NaCl, 0.2 g/l KCl, 1.5 g/l $Na_2HPO_4$ and 0.2 g/l $KH_2PO_4$), 0.1 ml of fresh medium A was added thereto, followed by culturing at 37° C. for 72 hours in the carbon dioxide gas incubator. Then, the culture supernatant was removed and 0.1 ml of a medium comprising medium A and 0.02% Neutral Red was added to the residue, followed by culturing at 37° C. for one hour in the carbon dioxide gas incubator, thereby staining the cells. After removal of the culture supernatant, the residue was washed once with physiological saline. Then, the pigment was extracted with 0.001 N hydrochloric acid/30% ethanol and absorbency at 550 nm was measured with a microplate reader. By comparing the absorbency of intact cells with that of the cells treated with a test solution having a known concentration, a concentration of the test solution which inhibited 50% of growth of the cells ($IC_{50}$) was calculated. The results are shown in Table 2.

(2) $HelaS_3$ cells $HelaS_3$ cells ($3 \times 10^4$ cells/ml) prepared in a medium comprising MEM medium (manufactured by Nissui Pharmaceutical Co., Ltd.) and 2 mM glutamine were put into wells of a 96 well microtiter plate in the amount of 0.1 ml per each well. In a manner similar to the case of MCF 7 cells described above, $IC^{50}$ was calculated. The results are shown in Table 2.

TABLE 2

| Test Compound | $IC_{50}$ (μg/ml) | |
|---|---|---|
| | MCF 7 cells | $HelaS_3$ cells |
| UCN-1028A | 0.21 | 0.29 |
| UCN-1028C | 0.18 | 0.19 |
| Phleichrome | 0.70 | 0.61 |

A process for producing UCN-1028A and UCN-1028C is described below.

UCN-1028A and/or UCN-1028C can be obtained by culturing a UCN-1028A and/or UCN-1028C-producing strain belonging to the genus Cladosporium in a medium and recovering UCN-1028A and/or UCN-1028C from the culture. As the UCN-1028A and/or UCN-1028C-producing strain, any strain can be used as long as it belongs to the genus *Cladosporium* and is capable of producing UCN-1028A and/or UCN-1028C. A representative strain, is KAC-2215 strain isolated by the present inventors from outdoor block walls in Osaka City.

Taxonomical properties of KAC-2215 strain are as follows.

When cultured at 20° C. using malt extract agar medium, a diameter of colony reaches 5.5 to 6 cm in 3 weeks. The center of the colony surface is grayish green and its circumference is gray. The back surface of the colony is dark greenish black. Hyphae are septate and extend in and on the medium. The hyphae are 1.5 to 5 μm in diameter and well branched. Conidiophore is brown or dark brown, is septate and stands from hypha. Conidia in chains develop on conidiophore or its ramoconidia. Mode of ontogeny in conidia is of budding type and the youngest conidium is located at the tip of conidial chain. Ramo-conidia located at the tip of conidiophore are composed of 1 to 2 cells in a width of 3 to 4 μm. One-celled conidia are oval, lemon-like shape or ellipsoidal and pale brown, and have a length of 4 to 6 μm and a width of 3 to 4 μm.

As a result of the foregoing observations, this strain was identified as *Cladosporium cladosporioides*. Microbiological properties of *Cladosporium cladosporioides* are described in Ellis, "Dematiaceous hyphomycetes" (1971).

The above strain has been named *Cladosporium cladosporioides* KAC-2215 and deposited with the Fermentation Research Institute, Agency of Industrial Science and Technology under FERM BP-1285 on February 10, 1987.

Fungi used in the present invention can be cultured by methods used for culturing ordinary molds. As the medium for culturing, either a natural medium or a synthetic medium can be used so long as it appropriately contains carbon sources, nitrogen sources, inorganic materials, etc. As the carbon source, glucose, starch, glycerol, mannose, fructose, sucrose, molasses, hydrocarbons, alcohols such as methanol and ethanol, organic acids such as succinic acid and acetic acid, etc. can be used. As the nitrogen source, ammonium chloride, ammonium sulfate, ammonium nitrate, sodium nitrate, urea, peptone, meat extract, yeast extract, dry yeast, corn steep liquor, soybean powder, Casamino acid, etc. can be used. As the inorganic materials, sodium chloride, potassium chloride, ferrous sulfate, zinc sulfate, manganese sulfate, copper sulfate, calcium carbonate, phosphates, etc. can be used. In addition, substances which accelerate the production of UCN-1028A and/or UCN-1028C such as biotin and vitamins, may also be supplemented to the medium.

As the culture method, either liquid culture or solid culture may be used, but usually liquid culture, especially submerged stirring culture, is used. Culturing temperature is 20° to 35° C., preferably 23° to 28° C. It is desirable to maintain the pH of the medium at 4 to 10, preferably 5 to 7 by adding aqueous ammonia, aqueous ammonium carbonate, etc. to the medium. Usually, by liquid culture for 1 to 7 days, UCN-1028A and/or UCN-1028C are produced and accumulated in the culture. When the amount of the products in the culture reaches the maximum, the culturing is discontinued and UCN-1028A and/or UCN-1028C are isolated and purified from the culture.

For the isolation and purification of UCN-1028A and/or UCN-1028C from the culture, an ordinary method for isolating a microbial metabolite from the culture can be utilized. For example, the culture is separated into the culture broth and the microbial cells by filtration, centrifugation, etc. The microbial cells are extracted with a solvent capable of dissolving UCN-1028A and/or UCN-1028C such as chloroform and acetone. The extract is concentrated under reduced pressure to remove the solvent, and the residue is dissolved in water to make an aqueous solution. The cell-free culture broth and the solution obtained by treating the microbial cells are treated with a non-ionic porous resin, for example, HP-20 (manufactured by Mitsubishi Chemical Industries Ltd.) to adsorb the active component on the resin. Then, the active component is eluted with methanol. After the eluate is concentrated, UCN-1028A and/or UCN-1028C can be isolated by extraction with a solvent such as ethyl acetate and/or column chromatography using a carrier such as a gel filtering agent and silica gel.

Certain specific embodiments of the present invention are illustrated by the following example.

EXAMPLE 1

*Cladosporium cladosporioides* KAC-2215 strain was used as the seed strain. One loopful of this strain was inoculated into 50 ml of a seed medium having the following composition in a 300 ml-Erlenmeyer flask, followed by shaking culture at 25° C. for 72 hours.

Composition of the seed medium: 5 g/l peptone, 5 g/l Ebios (manufactured by Ebios Pharmaceutial Co.), 10 g/l glucose, 200 ml/l V-8 Vegetable Juice (manufactured by Campbell Japan), 3 g/l calcium carbonate (pH 6.0, adjusted with NaOH prior to sterilization)

The resulting seed culture was transferred to 18 l of a fermentation medium having the following composition in 30 l-jar fermentor in the rate of 5% (volume) and cultured at 25° C. with aeration and stirring (rotation : 350 r.p.m,, aeration: 18 l/min).

Composition of the fermentation medium: 50 g/l soluble starch, 20 g/l dry yeast, 0.5 g/l KH2P04, 0.5 g/l MgSO4.7H2O, 5 g/l calcium carbonate (pH 7.0, adjusted with NaOH prior to sterilization)

Culturing was continued for 80 hours without controlling the pH.

The culture was filtered to separate microbial cells. To the microbial cells was added 30 of acetone and the mixture was stirred to extract UCN-1028A. After 90 of deionized water was added to the acetone extract, the solution was passed through a column packed with 2 of a non-ionic porous resin (HP-20; manufactured by Mitsubishi Chemical Industries Ltd.) to adsorb UCN-1028A thereon. Then impurities were eluted with 50% methanol solution, followed by elution of UCN-1028A with methanol. After the eluate was concentrated, the pH was adjusted to 1.7 and extraction was carried out with ethyl acetate. The ethyl acetate layer was concentrated and the concentrate was applied to 1 ( of silica gel (Wako Gel C-200; Wako Pure Chemical Industries, Ltd.) and developed with 1.5 ( of chloroform : methanol (99:1 v/v) to obtain fractions containing UCN-1028A. The fractions were concentrated and the concentrate was passed through a column packed with 300 m( of a non-ionic porous resin (HP20-SS; manufactured by Mitsubishi Chemical Industries, Ltd.). After the column was washed with 50% methanol solution, the concentrate was eluted with 70% methanol, 90% methanol and 100% methanol (1 l each) to give fractions containing UCN-1028A. The eluate containing the component was concentrated, and the concentrate was subjected to Sephadex LH20 column chromatography, followed by elution with methanol. Fractions containing the active substance were concentrated to give UCN-1028A (8.2 mg).

During the culturing and purification steps, UCN-1028A was traced by inhibitory activity on protein kinase C and a reddish orange spot of UCN-1028A by thin layer chromatography.

EXAMPLE 2

The same procedure as in Example 1 was repeated except that the silica gel chromatogram was developed with 1.5 l of chloroform : methanol (99 : 1 v/v) and subsequently with 1.5 l of chloroform : methanol (97 : 3 v/v), and as a result, 647 mg of UCN-1028C was obtained.

What is claimed is:

1. UCN-1028A or UCN-1028C represented by the following formula:

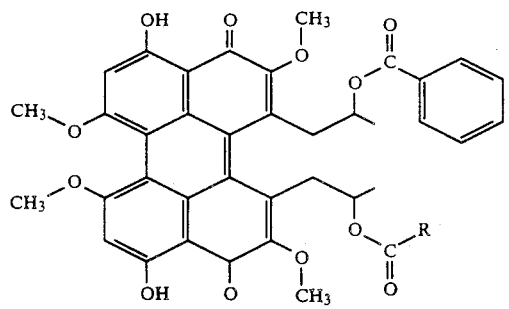
wherein R represents 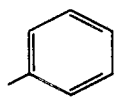 (UCN-1028A) or
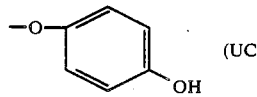 (UCN-1028C).
2. UCN-1028A represented by the following formula:
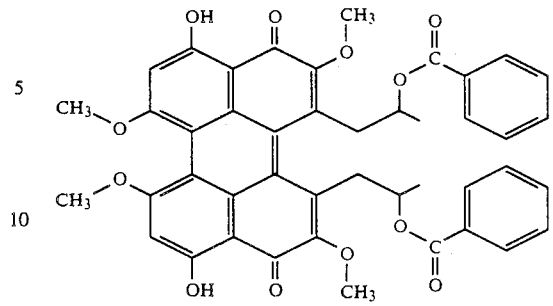
3. UCN-1028C represented by the following formula:
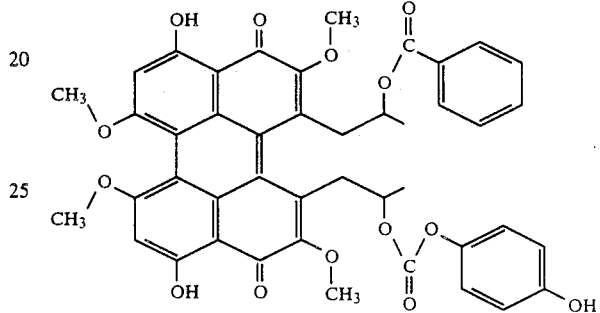
* * * * *